(12) United States Patent
Cantrell et al.

(10) Patent No.: US 10,414,715 B1
(45) Date of Patent: Sep. 17, 2019

(54) **METHODS FOR EXTRACTING AND PURIFYING CAPSINOIDS SUCH AS CAPSIATE AND DIHYDROCAPSIATE FROM *CAPSICUM* SP. FRUIT**

(71) Applicant: The United States of America, as Represented by the Secretary of Agriculture, Washington, DC (US)

(72) Inventors: Charles L. Cantrell, Oxford, MS (US); Robert L Jarret, Griffin, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/171,953

(22) Filed: Oct. 26, 2018

(51) Int. Cl.
    *C07C 67/58* (2006.01)
    *C07C 67/56* (2006.01)

(52) U.S. Cl.
    CPC .............. *C07C 67/58* (2013.01); *C07C 67/56* (2013.01)

(58) Field of Classification Search
    CPC ................................ C07C 67/58; C07C 67/56
    See application file for complete search history.

(56) References Cited

FOREIGN PATENT DOCUMENTS

EP      1772065    *    4/2007

* cited by examiner

*Primary Examiner* — Yevgeny Valenrod
*Assistant Examiner* — Blaine G Doletski
(74) *Attorney, Agent, or Firm* — G. Byron Stover; John D. Fado

(57) ABSTRACT

Disclosed are methods of extracting and purifying capsinoids (e.g., capsiate, dihydrocapsiate) from *Capsicum* species fruit involving drying (e.g., freeze drying) the fruit to produce dried fruit and grinding the dried fruit to produce powdered fruit, extracting the powdered fruit at least once with a non-polar organic solvent (e.g., pentane, hexane, heptane, iso-octane, cyclohexane) to produce an organic solvent extract, subjecting the organic solvent extract at least once to liquid/liquid extraction (partitioning; no drying involved) using a polar solvent (e.g., acetonitrile, methanol) to form a capsinoid enriched polar solvent partition, and optionally purifying the capsinoid enriched polar solvent partition (e.g., via HPLC using acetonitrile as a carrier) to yield capsinoids. The non-polar organic solvent is not miscible with the polar solvent.

9 Claims, 4 Drawing Sheets

METHODS FOR EXTRACTING AND PURIFYING CAPSINOIDS SUCH AS CAPSIATE AND DIHYDROCAPSIATE FROM *CAPSICUM* SP. FRUIT

BACKGROUND OF THE INVENTION

Disclosed are methods of extracting and purifying capsinoids (e.g., capsiate, dihydrocapsiate) from *Capsicum* species fruit involving drying (e.g., freeze drying) the fruit to produce dried fruit and grinding the dried fruit to produce powdered fruit, extracting the powdered fruit at least once with a non-polar organic solvent (e.g., pentane, hexane, heptane, iso-octane, cyclohexane) to produce an organic solvent extract, subjecting the organic solvent extract at least once to liquid/liquid partitioning (no drying involved) using a polar solvent (e.g., acetonitrile, methanol) to form a capsinoid enriched polar solvent partition, and optionally purifying the capsinoid enriched polar solvent partition (e.g., via HPLC using acetonitrile as a carrier) to yield capsinoids. The non-polar organic solvent is not miscible with the polar solvent.

Capsaicinoids (the pungency factor in hot peppers) are vanillylamide moieties with $C_9$-$C_{11}$ branched chain fatty acids. Capsaicin (FIG. 1) is widely used in the pharmaceutical industry as a result of its various biological properties, including its ability to increase metabolic activity.

A family of capsaicinoid-related compounds called capsinoids was reported in 1998 (Kobata, K., et al., J. Agri. Food Chem., 46(5): 1695-1697 (1998)). Principle among these is capsiate and dihydrocapsiate (FIG. 1) which was first isolated from the pepper (*Capsicum annuum* L.) cultivar CH-19 (Kobata et al., 1998). Capsinoids are similar in structure to capsaicinoids but possess an ester group in place of the amide moiety. As a result of this structural change, capsinoids are not pungent and they do not have the adverse side-effects typically associated with capsaicin: application of capsaicin to the skin and its ingestion often result in severe irritation. Naturally-occurring capsinoids include capsiate, dihydrocapsiate, and nordihydrocapsiate (Kobata, K., et al., J. Nat. Prod., 62(2): 335-336 (1999)).

The scientific literature suggests that capsinoids possess various forms of biological activity similar to those of capsaicin and its analogs. For example, reports indicate that capsinoids enhance adrenal catecholamine secretion, promote energy metabolism, suppress body fat accumulation, and increase endurance (Onuki, K., et al., J. Nut. Sci. and Vit., 47(4): 295-298 (2001a); Onuki, K., et al., Bio., Biotech., and Biochem., 65(9): 2033-2036 (2001b); Onuki, K., et al., Bio., Biotech., and Biochem., 65(12):pp. 2375-2 (2001c); Haramizu S., et al., BioSci. Biotechnol. Biochem., 70(4): 774-781 (2006); Faraut, B., et al., Intnl. J. Obesity, 33:1348-1355 (2009)). Capsiate improves glucose metabolism by improving insulin sensitivity (Kwon, D. W. Y., et al., J. Nutr. Biochem., 24: 1078-1085 (2013)). Capsiate has been shown to be more effective than capsaicin in delivering the analgesic drug N-ethyl-lidocaine (QX-314). The use of capsaicin to transport QX-314 across membranes results in significant pain, whereas capsiate is equally as effective but causes no pain (Nakagawa, H., and A. Hiura, Austin Biomark Diagn., 1:4-9 (2014)). Like capsaicinoids, capsinoids possess significant antioxidant activity (Rosa, A., et al., J. Agri. Food Chem., 50: 7396-7401 (2002)).

We have developed a new method of effectively isolating capsinoids such as capsiate and its analogs from fruit of *Capsicum* species such as *C. annuum* L.

SUMMARY OF THE INVENTION

Disclosed are methods of extracting and purifying capsinoids (e.g., capsiate, dihydrocapsiate) from *Capsicum* species fruit involving drying (e.g., freeze drying) the fruit to produce dried fruit and grinding the dried fruit to produce powdered fruit, extracting the powdered fruit at least once with a non-polar organic solvent (e.g., pentane, hexane, heptane, iso-octane, cyclohexane) to produce an organic solvent extract, subjecting the organic solvent extract at least once to liquid/liquid partitioning (no drying involved) using a polar solvent (e.g., acetonitrile, methanol) to form a capsinoid enriched polar solvent partition, and optionally purifying the capsinoid enriched polar solvent partition (e.g., via HPLC using acetonitrile as a carrier) to yield capsinoids. The non-polar organic solvent is not miscible with the polar solvent.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

Exemplary

Exemplary

Exemplary

Exemplary

DETAILED DESCRIPTION OF THE INVENTION

Figure 1:
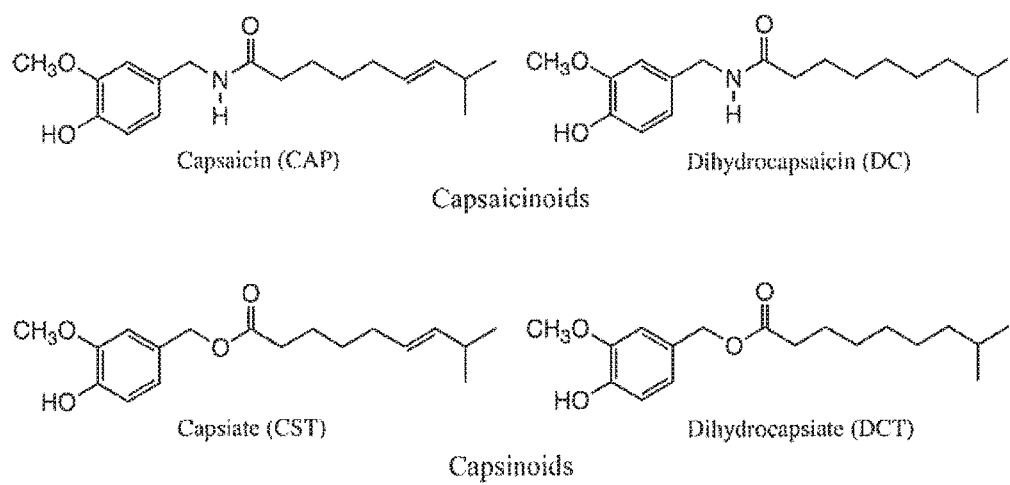
FIG. 1 shows the structures of capsaicinoids and capsinoids as described below.

Disclosed are methods of extracting and purifying capsinoids (e.g., capsiate, dihydrocapsiate) from *Capsicum* species fruit involving drying (e.g., freeze drying) the fruit to produce dried fruit and grinding the dried fruit to produce powdered fruit, extracting the powdered fruit at least once with a non-polar organic solvent (e.g., pentane, hexane, heptane, iso-octane, cyclohexane) to produce an organic solvent extract, subjecting the organic solvent extract at least once to liquid/liquid partitioning (no drying involved) using a polar solvent (e.g., acetonitrile, methanol) to form a capsinoid enriched polar solvent partition, and optionally purifying the capsinoid enriched polar solvent partition (e.g., via HPLC using acetonitrile as a carrier) to yield capsinoids. The non-polar organic solvent is not miscible with the polar solvent.

A general description of the methods is as follows: Generally the steps are performed at room temperature, although higher temperatures could be utilized. Dried fruit was ground to a fine powder in a large Waring commercial stainless steel blender. Powdered fruit (1.02 kg) was transferred equally to three 4L beakers. Plant material was covered with 1.5 L of pentane in each beaker and extracted at room temperature for about 24 hrs although the time could be more or less (e.g., about 12 hours to about 4 days (12 hours to 4 days), preferably about 18 hours to about 3 days (18 hours to 3 days), more preferably about 24 hours to about 2 days (24 hours to 2 days). Extractions were repeated three times although the total number of extractions could be more or less (e.g., 1 to 6, preferably 2 to 5, more preferably 3 to 4). Plant material was filtered using a large Büchner funnel and a 4 L vacuum filtering flask. Pentane was removed by rotary evaporation at about 35°C. yielding 83.33 grams of pentane extract. Liquid/liquid partitioning was done at room temperature on the pentane extract using approximately 20 grams of extract dissolved in 1 L of pentane (20 mg/mL) and extracted with 1 L of acetonitrile in a 4 L separatory funnel by shaking gently for about 1 to about 10 minutes although the time could be longer (e.g., up to 24 hours). This liquid/liquid extraction was repeated 4 more times although the total number of extractions could be more or less (e.g., 1 to 7, 2 to 6, 3 to 5) for a total of 81.05 grams of pentane extract processed. The pentane partition weighed 71.0 grams while the acetonitrile partition weighed 8.2 grams. The produced acetonitrile partition resulted in about 26.3% (wt/wt) capsiate and about 19.4% (wt/wt) dihydrocapsiate for a combined capsinoids yield of about 45.7% (wt/wt). The pentane partition contained only about 0.06% (wt/wt) capsinoids. No pH adjustments were necessary.

"Optional" or "optionally" means that the subsequently described event or circumstance may or may not occur, and that the description includes instances in which said event or circumstance occurs and instances where it does not. For example, the phrase "optionally adding a second non-polar organic solvent" means that the method may or may not involve adding a second non-polar organic solvent and that this description includes methods that involve and do not involve adding a second non-polar organic solvent.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

Examples

Production of fruit: Fifty plants of *Capsicum annuum* 509-45-1 (Plant Introduction 669378 in the USDA National Plant Germplasm System) were established in the greenhouse in April in Griffin, Ga., using peat pots filled with a standard potting mix. Plants were transferred to the field in June where they subsequently received fertilization and irrigation as required. Plants were spaced 24" apart in rows six feet apart. In October, entire plants were pulled from the ground and all completely green fruit were removed, bagged, and frozen at −20° C.

Drying of Fruit: Ten bags (approximately 1 kg of fruit each) were placed open in a Labconco FreeZone Legacy Freeze Dryer system. Fruit were allowed to dry for two weeks under vacuum at room temperature. Loss on drying was 81%, leaving approximately 190.0 g of dried fruit in each bag.

General Experimental: $^1$H and $^{13}$C NMR spectra were recorded on a Bruker Avance 400 MHz spectrometer (Bruker, Billerica, MA). NMR spectra were recorded in $CDCl_3$. HPLC analysis was performed on an Agilent 1260 system equipped with a quaternary pump, autosampler, diode-array detector, and vacuum degasser.

Crude Extractions of Dry Fruit: Experiment 1—Fruit were ground to a fine powder in a large Waring commercial stainless steel blender. The powder was transferred to 50 mL amber jars with a total dried powder weight of 192.92 g. Approximately 1 gram of powdered fruit were weighed into five 20 mL scintillation vials for extraction with 10 mL of the following solvents: hexane, chloroform, dichloromethane, ethyl acetate, and methanol. Extractions were repeated three times. Solvents were evaporated under a stream of $N_2$.

| 1st Crude Extraction Experiment | Weight of peppers used for extraction (grams) | Extract weight (mg) |
| --- | --- | --- |
| hexane | 1.069 | 120.2 |
| chloroform | 1.041 | 128.9 |
| dichloromethane | 1.041 | 131.7 |
| ethyl acetate | 1.034 | 133.7 |
| methanol | 1.059 | 341.4 |

Experiment 2—Using the same powdered material as the first experiment, approximately 1 gram of powdered fruit were weighed into six 20 mL scintillation vials for extraction with 10 mL of the following solvents: pentane, hexane, heptane, iso-octane, acetone, and 1-butanol. Extractions were repeated three times. Solvents were evaporated under a stream of $N_2$.

| 2nd Crude extraction experiment | Weight of peppers used for extraction (grains) | Extract weight (mg) |
| --- | --- | --- |
| pentane | 1.087 | 99.9 |
| hexane | 1.090 | 105.0 |
| heptane | 1.072 | 94.9 |
| iso-octane | 1.091 | 98.4 |
| acetone | 1.077 | 113.7 |
| n-butanol | 1.075 | 115.1 |

Steam Distillation of Peppers: Fresh fruit was steamed distilled to obtain an essential oil. Using a 3 L wide-mouth flask equipped with a Cleavenger apparatus and a heating mantle at 45% power, 652.26 grams of fruit in 1.2 L of deionized water was distilled overnight. The resulting essential oil obtained was 116.8 mg. The oil was prepared at 10 mg/mL in methanol for analysis on HPLC. There was no detectable capsiate or dihydrocapsiate in the essential oil.

Liquid/Liquid Extraction using Pentane/Acetonitrile—Concentration Variation: Approximately 10 gram of powdered fruit were weighed in duplicate in 250 mL beakers for extraction with 100 mL each of pentane. Extractions were repeated three times. Solvent was removed by rotary evaporation yielding approximately 1 gram of pentane extract each.

A liquid/liquid partitioning was done on the pentane extracts at two concentrations, 10 and 20 mg/mL. First, 1.0026 grams of extract was dissolved in 100 mL pentane (10 mg/mL concentration) and extracted two times with 100 mL acetonitrile in a 500 mL separatory funnel. Second, 1.0484 grams of extract was dissolved in 52 mL pentane (20 mg/mL) and extracted two times with 52 mL acetonitrile in a separatory funnel. Yields for the pentane and acetonitrile layers are in Table 3.

Liquid/Liquid Extraction using Pentane/Acetonitrile—Bulk Purification: Dried fruit was ground to a fine powder in a large Waring commercial stainless steel blender. Powdered fruit (1.02 kg) was transferred equally to three 4 L beakers. Plant material was covered with 1.5 L of pentane in each beaker. Extractions were repeated three times. Plant material was filtered using a large Büchner funnel and a 4 L vacuum filtering flask. Pentane was removed by rotary evaporation yielding 83.33 grams of pentane extract. Liquid/liquid partitioning was done on the pentane extract using approximately 20 grams of extract dissolved in 1 L of pentane (20 mg/mL) and extracted with 1 L of acetonitrile in a 4 L separatory funnel. This liquid/liquid extraction was repeated 4 more times for a total of 81.05 grams of pentane extract partitioned.

HPLC Quantitative Analysis. Capsiate and dihydrocapsiate analysis was performed as follows: approximately 20 mg of each extract was weighed in a 4 mL vial and prepared at 10 mg/mL in dichloromethane, in duplicate. The extracts were filtered using a 1 mL plastic syringe and a Millex 13 mm, 0.20 µm PTFE filter. The solvent was evaporated under a stream of $N_2$, leaving the organic soluble material to be dissolved in methanol (100%) and analyzed by HPLC. Extracts were analyzed using an HPLC system (Agilent 1260 series consisting of a vacuum degasser, quaternary pump, ALS autosampler, a diode array detector, and an Agilent Zorbax SB-C18, 4.6 mm×250 mm, 5 µm column). The injection volume for all samples and for the capsiate standard was 20 µL. An analytical gradient method was used (50% acetonitrile: 50% deionized water to 100% acetonitrile over 30 min and held at 100% ACN for 5 min) followed by a 5 minute re-equilibration. Analytes were detected at 280 nm.

Capsiate was purchased from Sigma-Aldrich (St. Louis, Mo.). Dihydrocapsiate was purchased from Santa Cruz Biotechnology (Dallas, Tex.). Individual concentration gradients were prepared for capsiate and dihydrocapsiate to obtain a standard curve using six concentration points imposed by using response factors and regression coefficients independently. Response factors (RF) were calculated using the equation RF=DR/C, where DR was the detector response in peak area (PA) and C was the analyte concentration. Confirmed integrated peaks were then used to determine the percentage of analyte in the extract. The RF of the target chemical constituent was used to determine the "percent" for each sample using the equation: PA/RF/C×100=% (peak area/response factor/concentration, wt/wt) in the plant tissue.

We evaluated procedures for isolating capsiate and its analogs from fruit of the mutant *Capsicum annum* (509-45-1), a germplasm released by Jarret et al. (Jarret, R. L., et al., HortScience, 49:107-108 (2014)). Fruits were dried, ground, and subjected to a series of liquid extractions to determine the solvent that could provide the greatest recovery and purity of capsiate and dihydrocapsiate in the extracts. Solvents chosen for the initial evaluation were hexane, chloroform, dichloromethane, ethyl acetate, and methanol. Data can only be compared between samples within this experiment (Table 1). All solvents in this experiment except methanol performed similarly. Surprisingly, hexane provided the best purity at 3.346% and recovery at 4.022 mg of capsiate from 1 gram dried fruit.

In a second and similar experiment using another batch of fruit, the experiment was expanded to include additional non-polar solvents. Solvents chosen for this experiment were pentane, hexane, heptane, iso-octane, acetone, butanol, and acetonitrile (Table 2). Also added was an essential oil produced from steam distillation. The essential oil contained no detectable capsiate or dihydrocapsiate and the butanol had low purity and recovery of capsiate. Surprisingly, pentane appeared to have the best combination of recovery and purity; however, the recovery in acetone was slightly higher than that observed for pentane.

From the above crude extraction results, it was hypothesized that it may be possible to start with a nonpolar crude extract such as pentane or hexane and selectively extract the capsinoids from this nonpolar extract using a more polar solvent such as methanol or acetonitrile to obtain a higher purity capsinoid partition. Liquid/liquid extractions were attempted using pentane as the nonpolar and methanol as the polar; however, surprisingly the miscibility of the two solvents could not be overcome despite the evidence that they should not be miscible. Hence this combination was not useful. Pentane therefore was chosen in combination with acetonitrile for purifications and scale-up trials. Surprisingly, the liquid/liquid extraction was possible directly following the crude extraction allowing for a quick transition to this step without the need to dry the pentane crude extract. Additional non-polar solvents that are not miscible with acetonitrile; non-polar solvents such as hexane, heptane, and cyclohexane could also be used successfully. Table 3 indicates the results from the liquid/liquid extraction using pentane/acetonitrile. The pentane layer was extracted using acetonitrile surprisingly providing a capsinoid-enriched fraction with 29% purity (wt/wt).

Two experiments were performed with the starting concentration of pentane extract at either 10 mg/mL or at 20 mg/mL. An equal volume of acetonitrile was then used for the liquid/liquid extraction step. From Table 3 it is clear at both concentrations that the capsinoids prefer the acetonitrile partition to the pentane partition. From Table 2 we know that the starting pentane extract contained about 2.5% (wt/wt) capsiate and 1.5% (wt/wt) dihydrocapsiate. Following extraction of this 10 mg/mL pentane extracted with acetonitrile, the resulting capsinoids purity is only 0.06% (wt/wt). Surprisingly, the acetonitrile partition was now 24.7% (wt/wt) capsiate and 22.7% (wt/wt) dihydrocapsiate for a combined capsinoids purity of 47% (wt/wt). Similarly, starting with a 20 mg/mL pentane extract, very little capsinoids were present in the pentane partition and 55% (wt/wt) were in the acetonitrile partition.

As a follow-up to the previous experiment, a scale-up experiment was also performed at the 20 mg/mL pentane extract concentration using 1 kg of plant material. Surprisingly, the produced acetonitrile partition resulted in 26.3% (wt/wt) capsiate and 19.4% (wt/wt) dihydrocapsiate for a combined capsinoids yield of 45.7% (wt/wt). Similar to the small-scale experiment, the pentane partition contained only 0.06% (wt/wt) capsinoids.

Figure 2:
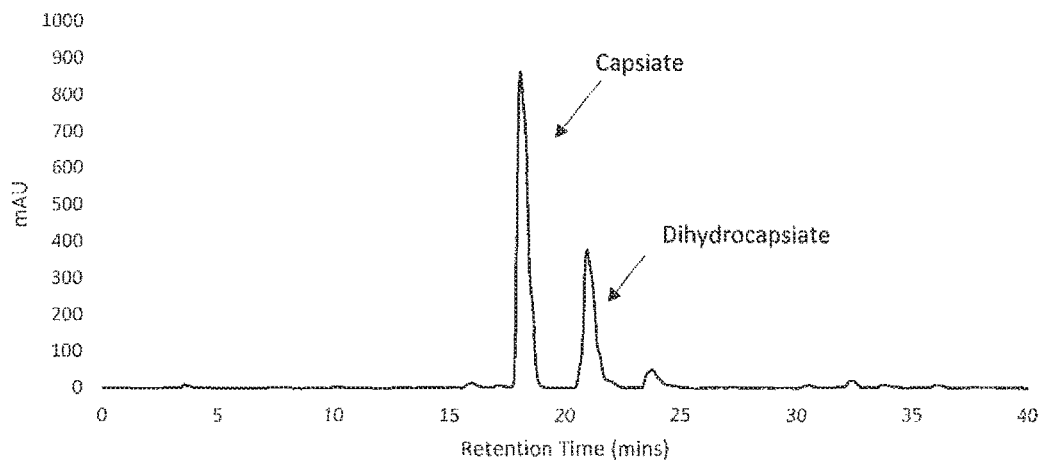
FIG. 2 shows HPLC analysis at 280 nm of the acetonitrile (ACN; top) and pentane (bottom) resulting from the liquid/liquid extraction procedure as described below.
Figure 2:
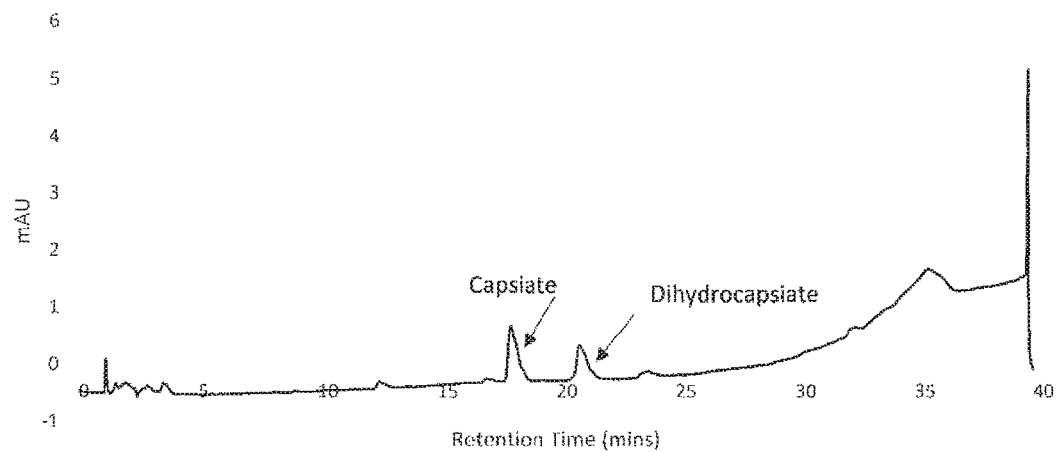
Figure 3:
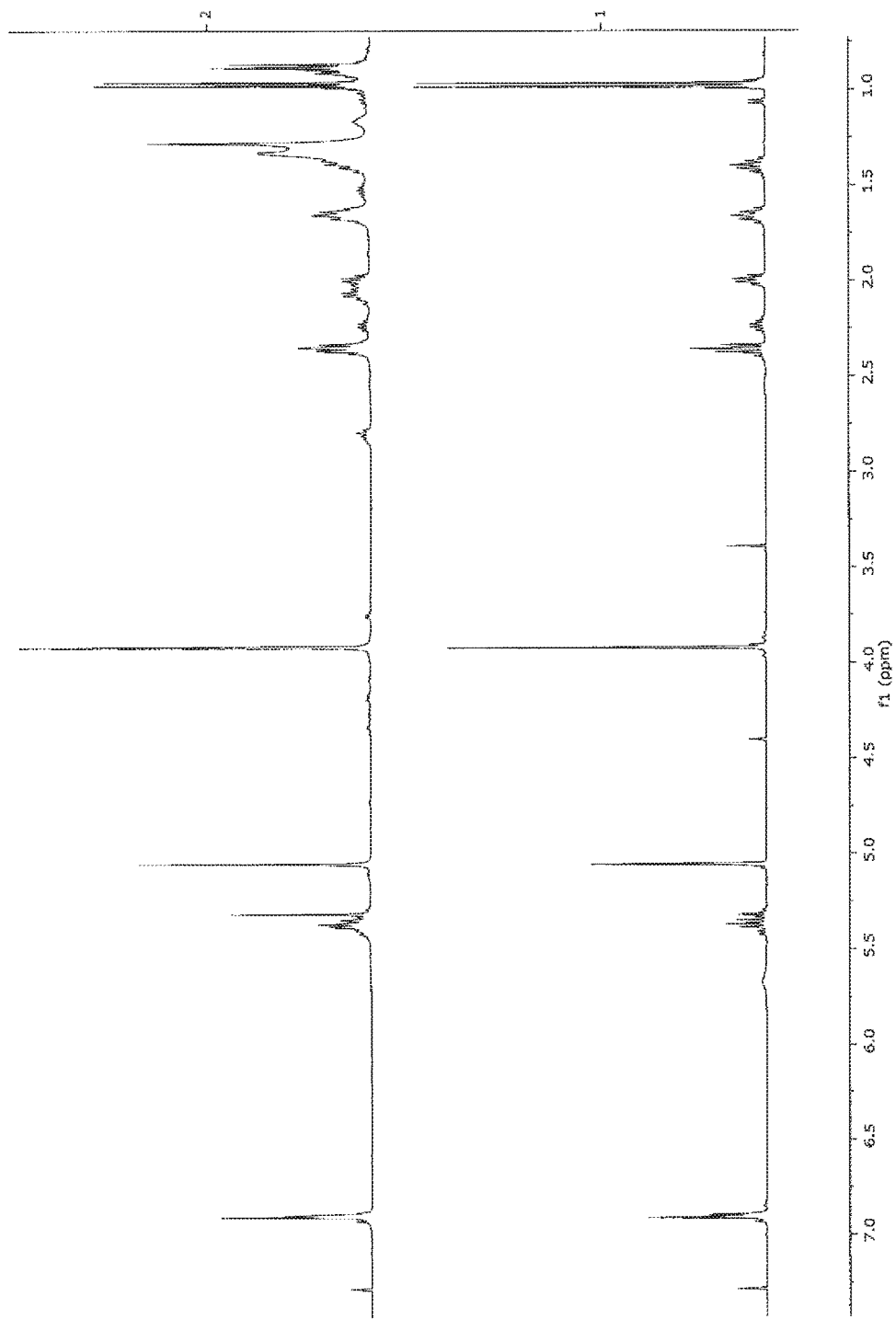
FIG. 3 shows $^1$H spectrum (400 MHz) of pure capsiate (bottom) and the acetonitrile partition product enriched in capsinoids (top) as described below.
Figure 4:
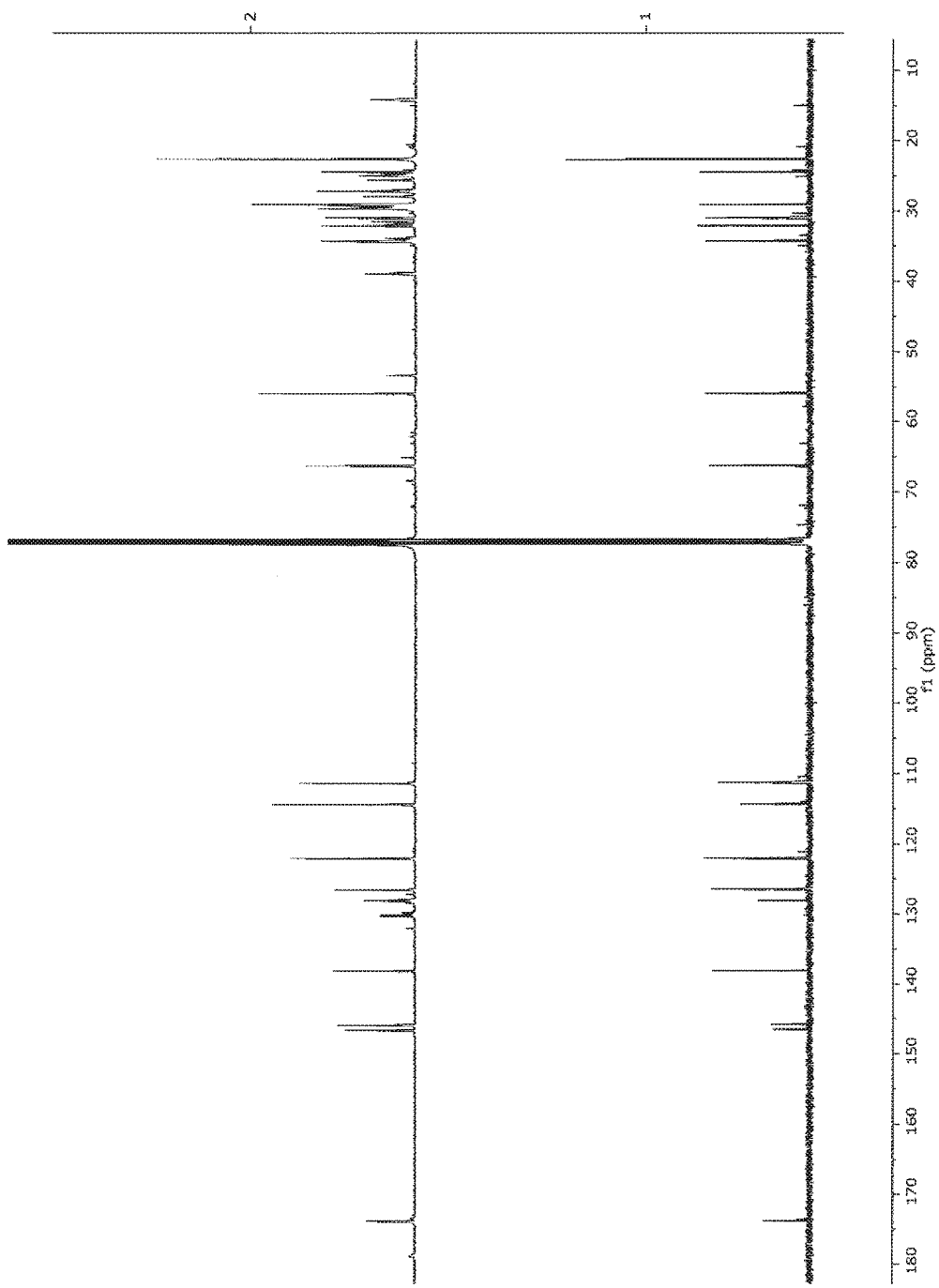
FIG. 4 shows $^{13}$C NMR spectrum (100 MHz) of pure capsiate (bottom) and the acetonitrile partition product enriched in capsinoids (top) as described below.

FIG. 2 demonstrates the HPLC analysis at 280 nm of the pentane and ACN partitions resulting from the liquid/liquid extraction procedure. Both samples were analyzed at the same concentration (10 mg/mL). Inspection of the y-axis indicates that the ACN layer has been enriched in capsinoids. Furthermore, $_1$H (FIG. 3) and $^{13}$C NMR (FIG. 4) analysis of partition clearly indicates the presence of the ACN layer with capsinoids as the spectra are nearly identical.

All of the references cited herein, including U.S. Patents and U.S. Patent Application Publications, are incorporated by reference in their entirety. Also incorporated by reference in their entirety are the following reference: U.S. Pat. No. 5,955,631.

Thus, in view of the above, there is described (in part) the following:

A method of extracting and purifying capsinoids from *Capsicum* species fruit, said method comprising (consisting essentially of or consisting of) drying said fruit to produce dried fruit and grinding said dried fruit to produce powdered fruit, extracting said powdered fruit at least once with a non-polar organic solvent (but not acetone since acetone is very polar and if acetone was used it would prevent the use of acetonitrile in the next step since these solvents are miscible) to produce an organic solvent extract, subjecting said organic solvent extract at least once to liquid/liquid partitioning using a polar solvent to form a capsinoid enriched polar solvent partition, and optionally purifying said capsinoid enriched polar solvent partition to yield capsinoids. The above method, wherein said *Capsicum* species is *Capsicum annum*. The above method, wherein said *Capsicum annum* is *Capsicum annum* 509-45-1. The above method, where said capsinoids are capsiate and/or dihydrocapsiate. The above method, wherein the yield of said capsinoids is over 45% (wt/wt). The above method, where said method does not involve use of a silver compound (e.g., silver nitrate, silver chlorate, silver perchlorate, silver acetate and silver sulfate). The above method, where said method comprises (consists essentially of or consists of) drying said fruit to produce dried fruit and grinding said dried fruit to produce powdered fruit, extracting said powdered fruit at least once with a non-polar organic solvent to produce an organic solvent extract, subjecting said organic solvent extract at least once to liquid/liquid partitioning using a polar solvent to form a capsinoid enriched polar solvent partition, and purifying said capsinoid enriched polar solvent partition to yield capsinoids.

A method of extracting and purifying capsinoids from *Capsicum* species fruit, said method comprising (consisting essentially of or consisting of) chopping fruit to produce chopped fruit, extracting said chopped fruit at least once with a non-polar organic solvent to produce an organic solvent extract, subjecting said organic solvent extract at least once to liquid/liquid partitioning using a polar solvent to form a capsinoid enriched polar solvent partition, and optionally purifying said capsinoid enriched polar solvent partition to yield capsinoids.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein. Thus, the specification includes disclosure by silence ("Negative Limitations In Patent Claims," AIPLA Quarterly Journal, Tom Brody, 41(1): 46-47 (2013): ". . . Written support for a negative limitation may also be argued through the absence of the excluded element in the specification, known as disclosure by silence . . . Silence in the specification may be used to establish written description support for a negative limitation. As an example, in *Ex parte Lin* [No. 2009-0486, at 2, 6 (B.P.A.I. May 7, 2009)] the negative limitation was added by amendment . . . In other words, the inventor argued an example that passively complied with the requirements of the negative limitation . . . was sufficient to provide support . . . This case shows that written description support for a negative limitation can be found by one or more disclosures of an embodiment that obeys what is required by the negative limitation . . . "

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Initial experiment to evaluate the efficiency of solvents at extracting capsiate from dried fruit of *Capsicum annum* (509-45-1).

| Extraction solvent | % Purity in crude extract | | Recovery (mg of analyte) from 1 gram dried fruit | |
|---|---|---|---|---|
| | capsiate | dihydrocapsiate | capsiate | dihydrocapsiate |
| hexane | 3.346 | 2.071 | 4.022 | 2.489 |
| chloroform | 2.914 | 1.905 | 3.757 | 2.548 |
| dichloromethane | 2.694 | 1.728 | 3.549 | 2.276 |
| ethyl acetate | 3.008 | 1.817 | 4.022 | 2.342 |
| methanol | 0.063 | 0.074 | 0.214 | 0.253 |

*Each experiment performed at x mg dry fruit/x mL solvent.

TABLE 2

A second experiment to evaluate the efficiency of solvents at extracting capsiate from dried fruit of *Capsicum annum* (509-45-1).

| Extraction solvent | % Purity in crude extract | | Recovery (mg of analyte) from 1 gram dried fruit | |
|---|---|---|---|---|
| | capsiate | dihydrocapsiate | capsiate | dihydrocapsiate |
| pentane | 2.510 | 1.537 | 2.508 | 1.536 |
| hexane | 2.280 | 1.390 | 2.394 | 1.459 |
| heptane | 2.315 | 1.437 | 2.196 | 1.364 |
| iso-octane | 2.197 | 1.370 | 2.162 | 1.348 |
| acetone | 2.370 | 1.511 | 2.695 | 1.718 |
| n-butanol | 0.611 | 0.523 | 0.703 | 0.602 |
| essential oil | 0.000 | 0.000 | 0.000 | 0.000 |
| acetonitrile | 2.832 | 2.099 | 2.415 | 1.790 |

*Each experiment performed at x mg dry fruit/x mL solvent.

TABLE 3

Concentration evaluation for performing liquid/liquid extractions of dry fruit

| Concentration | Partition | % Purity in partition | | Total % capsinoids |
|---|---|---|---|---|
| | | capsiate | dihydrocapsiate | |
| 10 mg/mL Experiment | pentane | 0.03 | 0.03 | 0.06 |
| | acetonitrile | 24.73 | 22.73 | 47.46 |
| 20 mg/mL Experiment | pentane | 0.03 | 0.04 | 0.07 |
| | acetonitrile | 29.34 | 25.76 | 55.10 |

We claim:

1. A method of extracting and purifying capsinoids from *Capsicum* species fruit, said method comprising drying said fruit to produce dried fruit and grinding said dried fruit to produce powdered fruit, extracting said powdered fruit at least once with a non-polar organic solvent to produce an organic solvent extract, subjecting said organic solvent extract at least once to liquid/liquid partitioning using a polar solvent to form a capsinoid enriched polar solvent partition, and optionally purifying said capsinoid enriched polar solvent partition to yield capsinoids.

2. The method according to claim 1, wherein said *Capsicum* species is *Capsicum annum*.

3. The method according to claim 2, wherein said *Capsicum annum* is *Capsicum annum* 509-45-1.

4. The method according to claim 1, where said capsinoids are capsiate.

5. The method according to claim 1, where said capsinoids are dihydrocapsiate.

6. The method according to claim 1, wherein the yield of said capsinoids is over 45% (wt/wt).

7. The method according to claim 1, where said method does not involve use of a silver compound.

8. The method according to claim 1, where said method comprises drying said fruit to produce dried fruit and grinding said dried fruit to produce powdered fruit, extracting said powdered fruit at least once with a non-polar organic solvent to produce an organic solvent extract, subjecting said organic solvent extract at least once to liquid/liquid partitioning using a polar solvent to form a capsinoid enriched polar solvent partition, and purifying said capsinoid enriched polar solvent partition to yield capsinoids.

9. A method of extracting and purifying capsinoids from *Capsicum* species fruit, said method comprising chopping fruit to produce chopped fruit, extracting said chopped fruit at least once with a non-polar organic solvent to produce an organic solvent extract, subjecting said organic solvent extract at least once to liquid/liquid partitioning using a polar solvent to form a capsinoid enriched polar solvent partition, and optionally purifying said capsinoid enriched polar solvent partition to yield capsinoids.

* * * * *